United States Patent [19]

Achener et al.

[11] 4,045,343

[45] Aug. 30, 1977

[54] HIGH PRESSURE LIQUID CHROMATOGRAPHY SYSTEM

[75] Inventors: Pierre Y. Achener; Detlef R. Boehme, both of Walnut Creek; Kenneth C. Judah, Napa; Miner N. Munk, Walnut Creek, all of Calif.

[73] Assignee: Varian Associates, Inc., Palo Alto, Calif.

[21] Appl. No.: 630,122

[22] Filed: Nov. 10, 1975

[51] Int. Cl.$^2$ .............................................. B01D 15/08
[52] U.S. Cl. ................. 210/101; 73/61.1 C; 210/198 C
[58] Field of Search ............ 210/31 C, 198 C, 96, 210/101; 55/386, 197; 73/61.1 C

[56] References Cited

U.S. PATENT DOCUMENTS

| | | | |
|---|---|---|---|
| 3,446,057 | 5/1969 | Bakalyar et al. | 210/31 C |
| 3,855,129 | 12/1974 | Abrahams et al. | 210/198 C |
| 3,917,531 | 11/1975 | Magnussen | 210/198 C |
| 3,934,456 | 1/1976 | Munk | 210/198 C |

OTHER PUBLICATIONS

Introduction to Modern Liquid Chromatography, by Snyder and Kirkland, John Wiley and Sons, New York, pp. 97-102.

*Primary Examiner*—John Adee
*Attorney, Agent, or Firm*—Stanley Z. Cole; John J. Morrissey; Gerald M. Fisher

[57] ABSTRACT

A high pressure liquid chromatography system including a reservoir for a liquid mobile phase, an LC column and detector, a high pressure reciprocating pump for enabling flow from said reservoir through the column, and a positively actuated inlet valve for controlling flow from the reservoir to the pump chamber. The pump is driven by motor means, such as a stepping motor, directly coupled thereto; and the inlet valve is actuated by the power train of the motor and pump, e.g., by an eccentric carried by the pump crank shaft. The pump piston is similarly driven by an eccentric, the pump and inlet valve eccentrics being angularly displaced in their respective positions at the crank shaft, as to delay opening of the inlet valve for a predetermined period following a pump stroke, so as to enable decompression of the liquid in the pump chamber.

21 Claims, 23 Drawing Figures

$\theta = \omega t$
$X = R \cos \omega t$

PISTON DISPLACEMENT
(R COS θ)

PISTON VELOCITY
(-R SIN θ)

FILL STROKE 278    PUMP STROKE 280

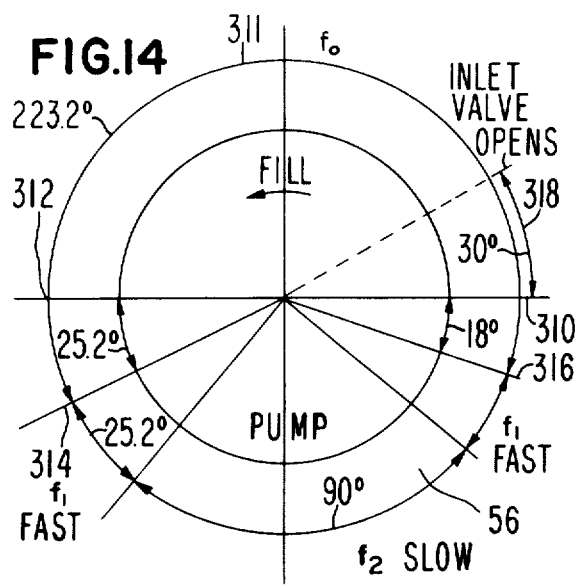
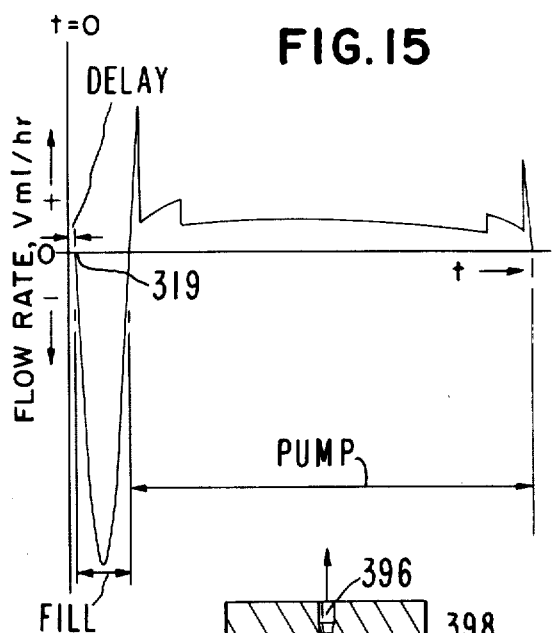
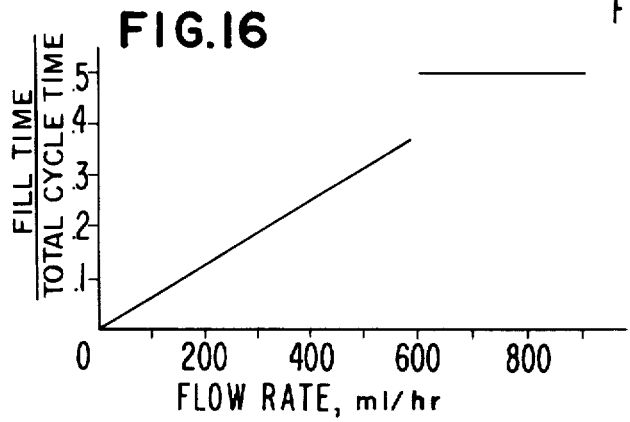
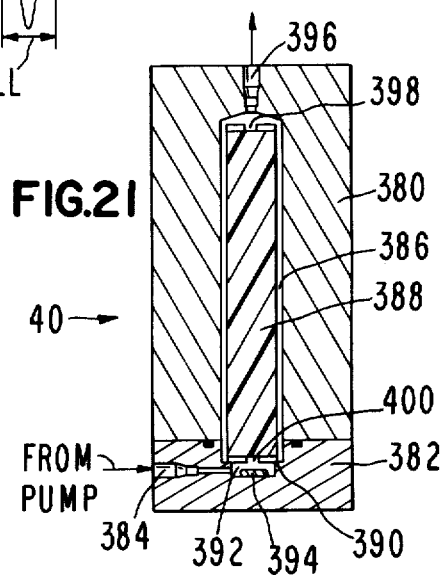
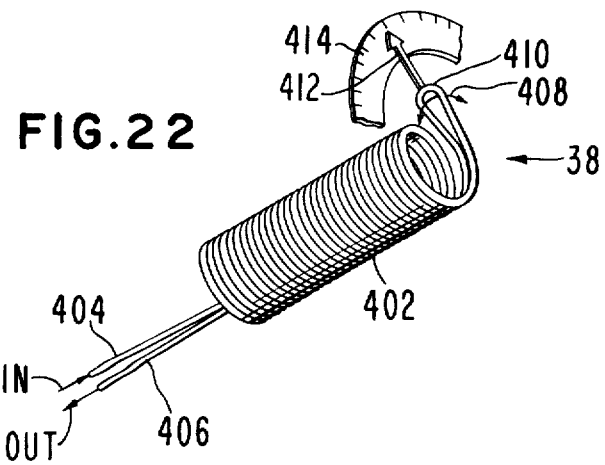

HIGH PRESSURE LIQUID CHROMATOGRAPHY SYSTEM

BACKGROUND OF INVENTION

This invention relates generally to liquid chromatography, and more specifically relates to a solvent supply system for use in high performance column liquid chromatography.

Chromatography is a separation method wherein a mixture of components (called the "sample" or "sample mixture") is placed as a zone at one end of a system containing a stationary phase and a mobile phase. Each component of the sample distributes itself in dynamic equilibrium between the two phases in a ratio characteristic of that component. As a result, the flowing mobile phase causes each individual component zone to migrate at a characteristic rate, and the zones become separated after a period of time.

There are various types of chromatography, e.g., liquid chromatography, gas chromotography, thin-layer chromatography, etc. The major differences between these various chromatographic methods lies in the physical state of the mobile phases (gas or liquid), and the manner in which the stationary phase is supported, e.g., coated on an inert granular material packed in a tube, coated on an inner wall surface, etc. In all these methods, the separation mechanism is essentially the same, i.e., distribution of the sample components between a mobile phase and a stationary phase. When the method is used for chemical analysis, a detector is commonly placed at the far end of the system to monitor the passage of the component zones as they emerge from the system. The signal from the detector is displayed on a recording device such as a strip chart recorder, and the record indicates both qualitative and quantitative information regarding the components of the sample.

It is often desirable for a chromatographic system to provide high resolution (i.e., a large degree of component separation with narrow zones), evenly spaced component zones, rapid separation, and a satisfactory record from a very small sample. The behavior of the system described in these terms may be called the "performance" of the system. It is well known in the chromatography art to improve system performance by changing one of the following system variables during the course of the analysis: temperature, chemical composition of the mobile phase, and flow rate of the mobile phase. For example, in gas chromatography the temperature of the system is often varied as a preselected function of time. This technique is known as "temperature programming", and it improves the performance of the system, especially with samples containing components which boil over a wide temperature range. Analogous to temperature programming in gas chromatography is the use of "gradient elution" in liquid chromatography. Gradient elution refers to changing the chemical composition of the mobile phase (also called the "eluent" or "eluting solvent") as a function of time, thereby improving the performance of the system, especially with samples containing components which vary widely in chemical properties. The net effect of gradient elution is to shorten the retention time of compounds strongly retained on the columns without sacrifice in separation of early eluting compounds. Further details regarding the fundamentals of gradient elution techniques may be found in numerous sources in the prior art, as, for example, in the publication by L. R. Snyder appearing in *Chromatograhy Review* 7, 1 (1965).

A central concern pertinent to liquid chromatography apparatus of the type considered herein, is one of providing a proper flow of solvent to and through the chromatographic column. Thus in the past, numerous and varied approaches have been utilized for supplying solvents to high performance liquid chromatographic columns. A key requirement in this connection is one of providing a relatively non-pulsating, (i.e., a constant) flow of solvent — in that the LC detector is sensitive to flow variations, and can provide erroneous readings and exhibit excessive noise in the presence of pulsating flow. Various approaches have been utilized in the past in order to enable such result; but in general, the prior art methodology directed at such end has involved highly expensive and overly complex mechanisms. Thus, in a typical example wherein a system is intended for operation in a gradient elution mode, i.e., by use of two distinct solvents, a dual cylinder pump arrangement has been utilized. Such an arrangement requires two distinct cylinder pumps, including separate means for driving each of the pumps, thus requiring separate speed controls, etc.

In principle, it would seem that many of the above-mentioned problems arising in connection with the solvent pumping systems of the prior art, might be overcome by use of a single cylinder arrangement in cooperation with a relatively small displacement volume reciprocating piston. A principal deterrent to the use of this arrangement, however, has been the fact that the ensuing flow will, by its nature, be pulsating — particularly at low flow rates. Further, the nature of the pulses present in the flow is such that they are not easily removed by filtering; and the presence of such pulses can sharply limit the efficiency of the detector system. It is understood in the foregoing connection that the word "piston" as used in the specification includes pistons where the seal remains fixed relative to the moving member and plungers where the seal is fixed with respect to the stationary cylinder.

It has in the foregoing connection been long recognized that the aspect of the reciprocating pump which is principally responsible for an unacceptable pulsating flow is the fact that, when the pump piston is driven by a simple crank shaft mechanism, the axial displacement of the piston as a function of time is sinusoidal. This implies, of course, the presence of equal time-spaced pressure (or liquid pumping) pulses, alternating with fill periods of duration equal to the pressure pulse duration for the pump chamber. In an effort to overcome this pattern, it has been proposed to drive the piston by suitably shaped cams. Pursuant to such approach, these cams serve to alter the time displacement function of the pump piston so as to foreshorten the fill portion of the cycle in comparison to the pumping portion of the cycle, and in some instances to render the movement during pumping relatively linear in nature, i.e., to render the displacement linear as a function of time. This sort of arrangement does have the advantage of changing the form of the pulsating pattern so as to diminish the pulsing and render filtering of the remaining pulses more feasible. However, this approach is less than satisfactory in a most important respect. In particular, the cam represents a fixed pattern, and thus provides a fixed relationship or ratio between the fill and pumping portions of the pump cycle. And yet, in many instances it is desired to have a capability for operation over various flow rates — which indeed can vary very widely. If, however, the flow rate is increased by merely increasing the rate of cam rotation, then the fill portion of the cycle becomes successively shortened — and can reach a point where insufficient feed time is available, leading to cavitation and other problems.

In a U.S. Pat. No. 3,985,021 granted to the present inventors, and entitled HIGH PERFORMANCE LIQUID CHROMATOGRAPHY SYSTEM, which patent is assigned to the same assignee as is the present application, there is disclosed a liquid chromatography system which is particularly useful in overcoming the aforementioned flow problems. The system described in that patent includes a reservoir for a liquid mobile phase, a liquid chromatographic column, reciprocating pumping means for pumping the mobile phase through the column, and motor means for driving the pumping means through successive reciprocation cycles. Means are provided further, for controlling the rotational speed of the motor throughout the reciprocation cycle of the pump so as to provide preselected average rotational speeds over predetermined subintervals of each successive reciprocation cycle. Application of the control cycle is synchronized with the pumping cycle so that the speed control is properly applied over each successive reciprocation cycle.

A further problem evidenced in the prior art, including in the systems of the type just considered, arises in connection with the inlet valve commonly utilized to control flow proceeding toward the pump chamber. In the past it has been common to use a simple check valve for such purpose, the valve usually being of the gravity-biased type. In practice, however, much difficulty has been experienced with such devices. In particular, the pressure difference across the check valve is so slight as to make operation unreliable — even minor amounts of particulate matter can severly impair operation of the valve. Further, the reliance on gravity to close the check valve creates another source of serious difficulties.

In accordance with the foregoing, it is an object of the present invention, to provide a high performance, high pressure liquid chromatography system incorporating an inlet valve structure for controlling flow to the system pump, wherein valve actuation is positive, thereby enabling high reliability in the operation of such valve, and completely accurate control of the opening and closing points thereof.

SUMMARY OF INVENTION

Now in accordance with the present invention, the foregoing objects and others as will become apparent in the course of the ensuing specification are achieved in a liquid chromatography system of the type including at least one reservoir for a liquid mobile phase, a liquid chromatographic column, and pumping means for directing the mobile phase through the column. The pumping means comprises a compact, relatively low cost unit based upon a rod-like reciprocating piston which undergoes movement in a small volume chamber. In the usual mode of operation, two or more distinct solvents are fed into the pump from separate reservoirs via proportioning valves which are actuated in complementary fashion over a selected part of the fill sub-cycle. These valves are thus positioned on the low pressure side of the fluid flow pattern. An inlet valve at the pump controls passage of the liquid mixture to the pumping chamber during the fill portion of the pump cycle. An advantage of an inlet valve of this type over a check valve is that the check valve is much more susceptible to causing cavitation within the pump, especially if spring-loaded shut, as compared to a positive mechanically operated construction. An additional advantage of such an inlet valve is its greatly reduced susceptibility to sticking in either the open or shut position, as compared to a check valve. Reciprocating movements of the rod-like piston and the inlet valve are effected through drive linkages, which in turn are actuated by a pair of eccentrics formed about the pump crank shaft.

The pump crank shaft is driven through a flexible coupling by means of a stepping motor. The stepping motor in the present environment has particularly noteworthy advantages, which arise from the fact that such device is susceptible of precise control by application of pulses at a controlled rate. Indeed, a steppng motor is susceptible of such control throughout its entire dynamic range — which is comparatively wide. In the presence of such pulse application, the motor thus undergoes a precise angular rotation, and at a relatively constant average speed.

The average rotational velocity of the stepping motor is controlled throughout each full crank shaft rotation, so as to enable a precisely selected cycle of pump operation. In particular, the speed of the motor is so regulated in conjunction with the mechanical actuation of the pump piston and inlet valve as to provide (at the low flow rates where such behavior is critical) a very short duration fill period — which implies a rapid withdrawal of the piston or plunger from the pump cylinder. Thereafter, the second portion of the pumping cycle, which corresponds to pumping or displacing the liquid from the pump toward the chromatographic column, is effected under crank shaft rotation (as a function of time) such that the axial displacement of the piston is relatively linear as a function of time.

In order to achieve the aforementioned linear piston displacement during the pumping part of the cycle, one may control the rate of drive pulse feed to the stepping motor so that the displacement of what is effectively the piston linkage drive point at the crank shaft has a component in the direction of piston displacement, which is approximately constant per unit time over the entire pump or pressure stroke of the piston. Since the average velocity of crank shaft rotation over the corresponding angular interval will be determined by reference to a suitable memory, one may, however, reduce the complexity and cost of the memory and attendant circuitry by sharply limiting the number of angular intervals to, e.g., five angular intervals. Over the course of each of these intervals, the average angular velocity of the crank shaft is thus maintained at a preselected value. While a greater degree of linearity can be achieved by increasing the number of angular intervals, and thus by increasing the numbers of rotational velocities assigned to such intervals, a relatively linear displacement function is yet enabled with the scheme indicated.

The angular velocity of the crank shaft during the fill portion of the cycle is maintained at a constant value, irrespective of the average rate of flow set for the pump. Where it is desired to increase the pumping rate, however, the rate of pulse application to the stepping motor is adjusted suitably through the pumping portion of the cycle, the appropriate rates being stored in a suitable memory which is accessed in response to the pumping rate set upon the apparatus. By virtue of maintaining the fill portion of the cycle constant, it will be evident that the ratio between fill and pump portions of the cycle increases with pump flow rate. At high flow rates, however, the pulsation problem effectively disappears; and indeed the present device is intended to assume a 50–50% time division between fill and pump portions of the cycle at such high flow rates.

An encoder wheel is coaxially mounted upon the pump crank shaft so as to rotate therewith. The encoder wheel is provided with a series of slots extending about its periphery. The spacing between slots is variable, and so correlated with the fill-pump cycle as to assure that successive pulses enabled by an optical reader occur in correspondence to equal stepwise axial displacements of the pump piston. Accordingly, one need only count pulses in order to derive a result indicative of piston position. This arrangement, further, enables a simple and accurate scheme for proportioning the solvents which are utilized during gradient elution work. In particular, a specific gradient setting, as manually or automatically determined, is set on the instrument with the corresponding information being provided to a comparator. During a portion of the fill cycle, a solenoid-activated valve controlling flow from a first reservoir is opened, while a second such valve (controlling flow from the second reservoir) is closed. The encoder disc interacting with a slot counter provides a signal to the comparator when the division point in the fill cycle is reached — which corresponds to the gradient setting. The comparator in turn (through the valve logic) controls the valve drivers for the pair of valves so that (at such division point) the first valve is closed and the second valve is opened, thus automatically proportioning the volumes of the respective solvents in accordance with the gradient setting.

Because the proportioning valves 28 and 30 are on the low pressure side of the pump 26, the reservoirs 22 and 24 are essentially at atmospheric pressure and are therefore fully accessible for filling. Where the reservoirs are at high pressure, a third reservoir is usually required — such as a holding coil. A further advantage of having the valves 28 and 30 operate at low pressure is that the valve construction can be of relatively low cost construction; or one can build higher reliability into the valve at a given cost where a requirement to withstand higher pressure is absent.

In accordance with a further aspect of the present invention, the mechanical linkage between the inlet valve and its driving eccentric includes an overtravel mechanism, which thus introduces a slight, and adjustable free play into such linkage. This feature enables a discontinuity in the valve movement, which is necessary in order to assure a finite closing period. The two eccentrics are angularly displaced with respect to one another so as to enable a slight delay period following the initiation of piston withdrawal and before the inlet valve opens. This delay enables decompression of that solvent not displaced from the cylinder during the pump stroke (cycle) as well as relaxation of compressible members in the pump cylinder and drive train. Were such slight delay not provided for, the aforementioned compression effects could cause transient flow reversal during such portion of the cycle.

BRIEF DESCRIPTION OF DRAWINGS

The invention is diagrammatically illustrated, by way of example, in the drawings appended hereto, in which:

FIG. 14 is a graphical representation generally similar to FIG. 11, and indicating a typical rotational velocity pattern utilized in connection with the present invention;

FIG. 15 illustrates the flow pattern achieved over a cycle of operation for a pump in accordance with the invention operating as in FIG. 14;

FIG. 16 is a graph of the ratio of fill time to total cycle time as a function of flow velocity for a typical system in accordance with the invention;

FIG. 17 is a perspective view of an encoding disc and related elements utilizable in the pump of FIGS. 2 and 3;

FIG. 18 is a schematic depicton indicative of the indicia distribution on the disc of FIG. 17;

FIG. 19 is a schematic depiction indicative of the relationship between indicia spacing and piston displacement, for the disc of FIGS. 17 and 18;

FIG. 20 is a partial plan view of another type of encoding disc utilizeable with the invention;

FIG. 21 is a longitudinal cross-sectional view through a damper utilizeable with the present system;

FIG. 22 is a simplified perspective view of a pressure monitor utilizeable with the invention.

DESCRIPTION OF PREFERRED EMBODIMENT

Figure 1:
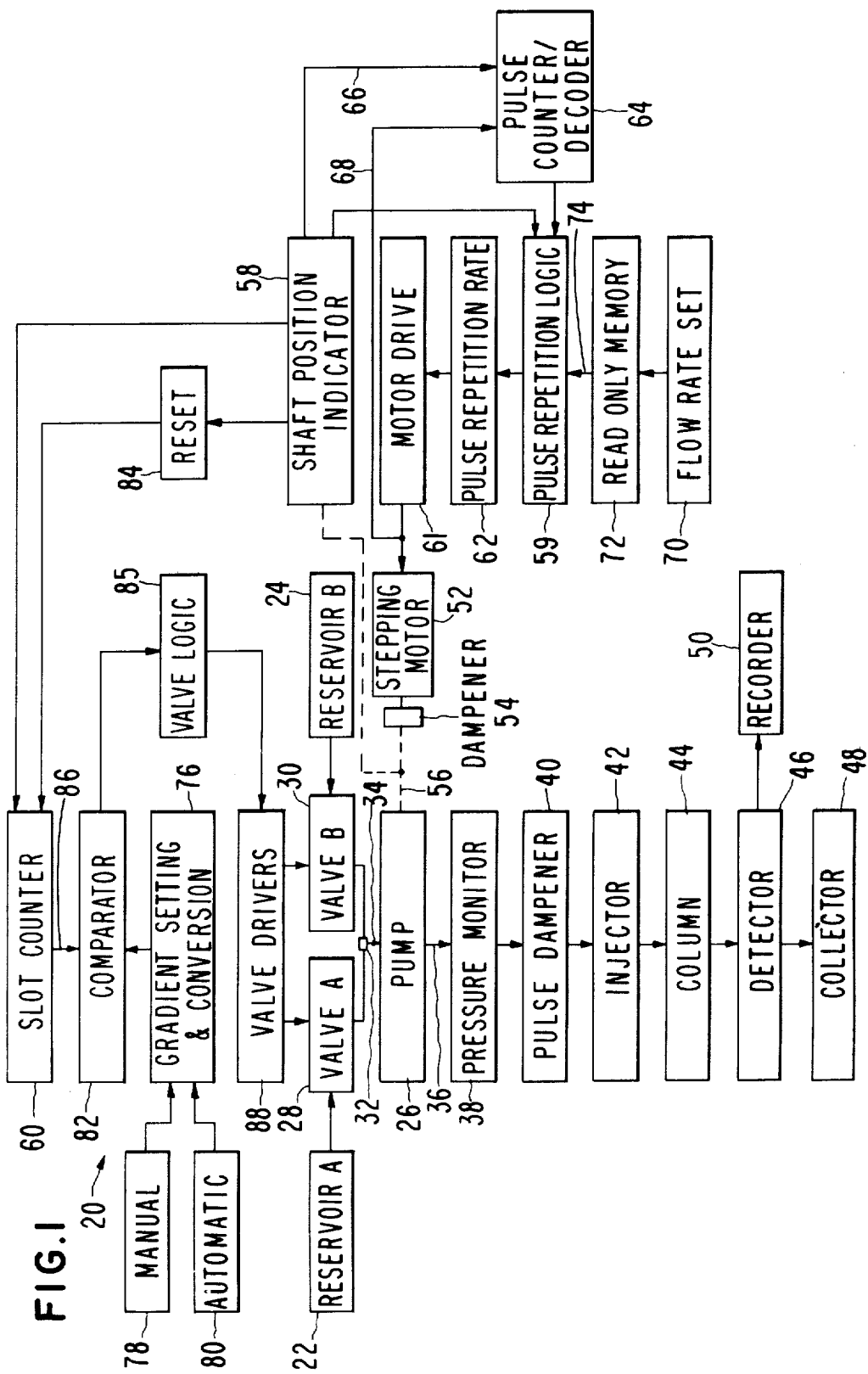
FIG. 1 is a simplified block diagram setting forth the basic elements, including the electrical control elements, of a chromatography system in accordance with the present invention.

In FIG. 1 herein a simplified block diagram appears setting forth the key elements forming part of the present liquid chromatography system. System 20 is illustrated for use with a pair of reservoirs 22 and 24, each of which contains a distinct solvent, as for example water on the one hand and methanol on the other. The reservoirs are identified for convenience in the Figure as "A" and "B". Each of the solvents is furnished to the pump 26 by means of an individual solonoid valve, either 28 or 30. Values 28 and 30 are associated, respectively with the reservoirs 22 and 24. These valves, which can be regarded as serving a proportioning function, are identified by designations "A" and "B" in correspondence to the reservoir identification. The liquids proceeding from valves 28 and 30 enter the mixing tee 32, which then furnishes the mixed solvent composition via line 34 to pump 26. The output 36 from the pump may be monitored by a pressure gauge or sensor 38; and safety devices, as for example a rupture disc, may be associated with the continuing inline flow in order to avoid any possibility of danger arising from excessive pressures — which pressures can be of the order of 5,000 psi or thereabouts. The flow then proceeds through a pulse damper 40, details of which will be subsequently set forth; and after passing through a conventional injector 42, the flow enters the liquid chromatographic column 44. The output from column 44, as is conventional, may be provided to a detector 46 and thence to a collector 48. Detector 46 may be associated with a suitable recorder 50, again as is known in the art.

In accordance with the invention, pump 26 is driven by a means of a stepping motor 52. Stepping motor 52 is per se conventional. Further, a conventional damper 54 may be associated with the stepping motor 52, as for example by being mounted to one end of the drive shaft of the motor. Dampers of this type, suitable for the present purposes, are produced by numerous manufacturers.

The angular rotational velocity of the stepping motor is accurately controlled throughout a 360° rotational cycle of its shaft, so as to thereby control the rotational velocity of pump crank shaft 56 which is coupled thereto. Accordingly, a shaft position indicator means 58 is provided, the shaft position indicator means being associated with shaft 56 in a manner as will be subsequently set forth. The shaft position indicator may thus include an encoding wheel provided with peripheral indicia such as slots, which are read by a slot counter 60 during shaft rotation.

The stepping motor 52 is driven by a motor drive 61, which as is known in the art of driving such motors, provides a series of successive electrical pulses to the stepping motor, which then rotates in steps in accordance with the rate of pulse input. In order to enable the stepping motor to be driven at differing average angular speeds in accordance with its angular position, the shaft position indicator 58 provides a reference signal to pulse repetition logic 59 upon the shaft 56 reaching a given point in its angular rotation. In turn, the pulse repetition rate 62 is suitably altered. At the same time, a pulse counter decoder 64 is enabled through control line 66 and begins to count successive pulses emanating from motor drive 61 via line 68. In the present instance, it will thus be noted that the count of drive pulses via line 68 serves as a determinant for the position of the shaft 56 rather than the shaft position indicator directly. This is advantageous because, as will be subsequently seen, some flexibility is present in the shaft; and it is considered that less possibility of error can occur by counting the successive pulses than by directly taking the reading from the shaft position indicator. In any event, the counter/decoder 64, having effectively determined the angular position of the shaft, converts the counted pulses to a decoded signal indicating to the pulse repetition rate source 62 the number of pulses per second which are appropriate for the then determined position of shaft 56.

In a preferred embodiment of the present invention, the flow output from pump 26 may vary over a considerable range, as for example from 10 milliliters per hour up to the order of 1,000 milliliters per hour. In order to enable the required variation in pumping speed, a flow rate set means 70 is provided, which may take the form of simple thumb switches. When a given flow rate is set at block 70, a preset programmed read only memory means 72, which has previously been provided with the program appropriate for the desired flow rate, provides the specified program for each portion of the cycle of operation to the pulse repetition logic 59 via line 74, the logic then controlling the repetition rate accordingly.

As has previously been indicated, in a typical mode of operation of the present system, two solvents may be utilized. The ratio between the two solvents may in some instances be maintained at a relatively constant value; but more commonly the ratio between solvents will vary over the course of a test run, either by manual resetting of the ratio or by automatically controlled programmed changes. A gradient setting and conversion means 76 is thus provided, which may either have a manually controlled input setting 78 or may be provided with an automatic gradient program from means 80. Gradient programming, as has been previously indicated, is per se conventional; and accordingly, details of such devices are not set forth herein.

The output from gradient setting means 76, after conversion to a suitable manipulatable form, is provided to a comparator 82. The numerical count from slot counter 60 is reset once each cycle by reset means 84 upon a reference point being determined during shaft rotation by shaft position indicator 58. When the slot counter 60 output, proceeding via line 86 to comparator 82, equals the converted value provided by gradient setting and conversion means 76, an enabling signal is provided to valve logic 85, which actuates valve drivers 88. These control the opening and closing of valves 28 and 30, which as has been previously mentioned, operate in substantially complementary fashion — in the sense that when one is open the other is closed. It will thus be evident that by means of the present arrangement one of the valves may be open throughout a portion of the fill cycle for the pump 26 while the other valve is closed, and that throughout the remainder of the fill cycle the reverse is true, i.e., the second valve is open while the first valve is closed. Thus direct proportioning of the solvent mixture is determined in a very simple manner by deriving control signals in accordance with the angular position of the pump drive shaft, and utilizing the signals to divide a subcycle time between feed from the first and second valve in accordance with the gradient setting then appropriate. These aspects of the invention will be further elucidated hereinbelow, in connection with the cycle and time diagrams of FIGS. 14, 15 and 23.

Figure 2:
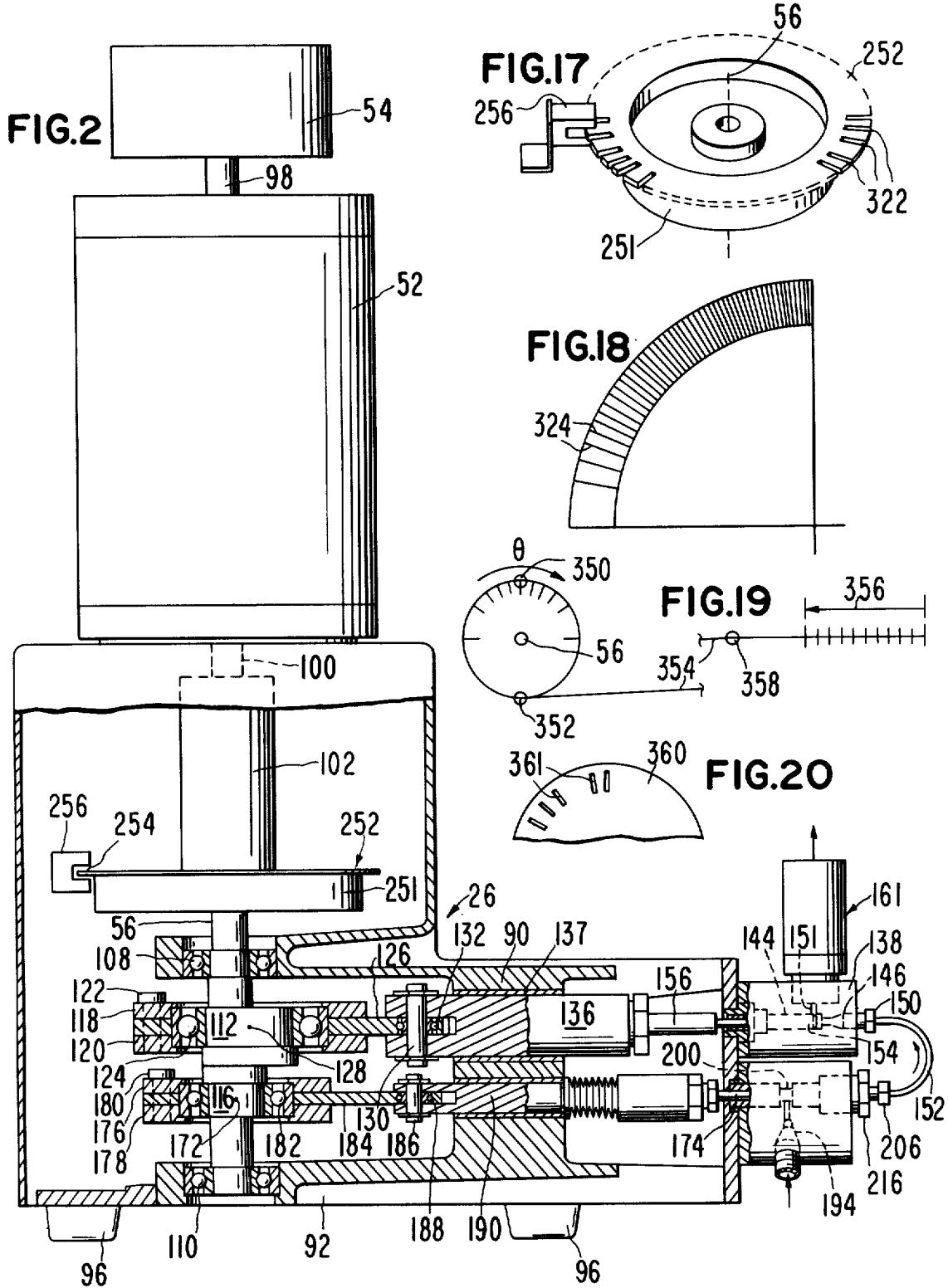
FIG. 2 is an elevational view, partially broken away and sectioned, setting forth key elements of the pump and related mechanical components of the present system.
Figure 3:
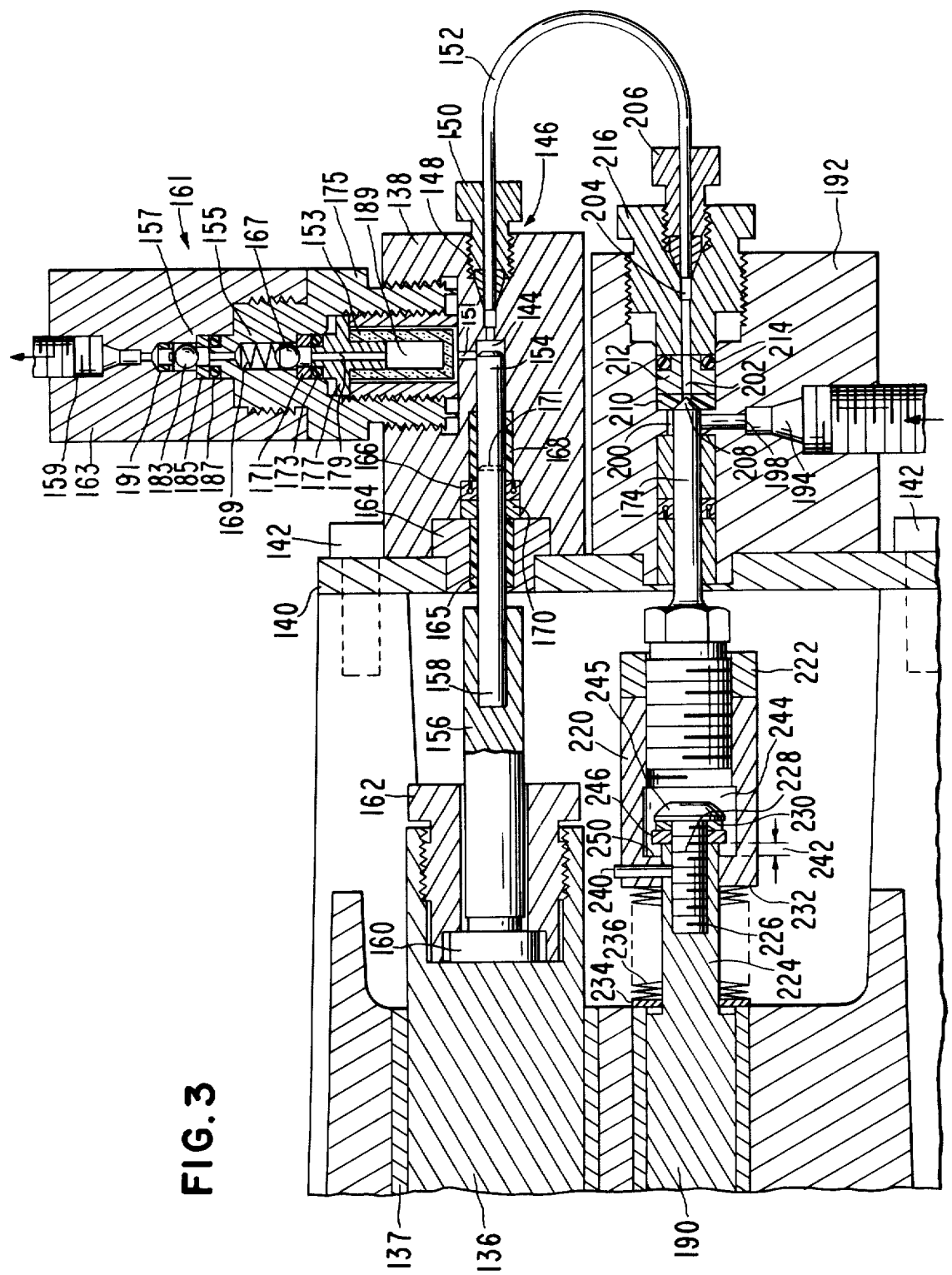
FIG. 3 is an enlarged longitudinal sectional view through those portions of the FIG. 2 apparatus residing to the right of the pump crank shaft, such view therefore including details of the inlet housing and of the pump head portion of the present device.

In FIG. 2 an elevational, partially broken away, and sectioned view appears of the pump 26; in addition, the stepping motor 52 and damper 54 associated with the pump appear. This Figure may be considered simultaneously with FIG. 3, which enlarges certain portions of the FIG. 2 showing. The several elements mentioned are mutually associated through means of a frame 90, which may comprise an aluminum casting. The frame is provided at its bottom portion 92 with rubber mountings 96, which are secured to bottom portion 92 by means of fasteners passing through threaded openings in the mountings.

As has been previously indicated, stepping motor 52 has secured to the upwardly extending portion 98 of its shaft the damper 54 already described. The downwardly extending portion 100 of the motor drive shaft passes into a flexible coupling 102, by means of which the motor shaft is coupled to the pump crankshaft 56. The flexible coupling 102 is per se a conventional device, which in the present instance is of the gear grip type. The flexible coupling 102 basically consists of a pair of metal collars which are internally toothed or knurled to enable engagement with the shafts entering each end of the coupling, with a rubber sleeve passing between the two collars. Set screws may pass transversely through the metal collars as to fix the position of the coupling with respect to the shafts. The principal purpose of the flexible coupling herein is to isolate vibrations. These vibrations occur in consequence of intermittent operation of stepping motor 52, a phenomenon which is further itensified by the relatively abrupt speed changes which occur in the operation of stepping motor 52 in accordance with the present invention.

It may be pointed out here that the coupling between the drive shaft and the pump crank shaft 56 is direct, i.e., no gear reduction is utilized. This is partially a result of proper selection of the stepping motor, i.e., with respect to torque output and speed characteristics, but is also in consequence of the quite small piston utilized in the pump and of the very small liquid displacement per pump stroke.

Pump shaft 56 is seen to be journaled for rotation within frame 90 by a pair of ball bearings 108 and 110. The shaft 56 further carries a pair of eccentrics, namely, a pump eccentric 112 and an inlet valve eccentric 116. These two eccentrics, each of circular cross-section, respectively drive the linkages for actuation of the pump piston and of the inlet valve.

Referring firstly to pump eccentric 112, it is seen to consist of the yoke pieces 118 and 120, which are secured to one another through assembly bolts such as at 122. As eccentric 112 rotates, the yoke 118 rotating about a ball bearing 124 displaces the connecting link 126 toward and away from the axis of rotation of the crankshaft. The connecting link 126 is in turn connected to wrist pin 130, which is mounted within a ball bearing 132. The wrist pin 130, in turn, is transversely mounted to a slider member 136, which can undergo reciprocating motion within a bronze bushing 137 inserted into frame casting 90.

The actual pumping chamber in the present arrangement is formed in a pump head 138, which is secured through a plate 140 to the frame 90 by means of threaded fasteners 142. Thus, the pump chamber 144 is seen to be formed as a small cylindrical cavity in pump head 138. One end of this cavity communicates with a fluid inlet 146, which receives the mixture of solvents flowing into the chamber during an appropriate portion of the pump cycle. Inlet 146 is threaded as at 148, to receive a threaded compression fitting 150, which is in turn associated with a flexible conduit 152 for the liquid being pumped. The piston 154 for the pump, specifically comprises a cylindrical rod which may be tapered at its forward end, the rod preferably being formed of sapphire. The sapphire rod, in addition to having very smooth surfaces and therefore sliding readily in the pump chamber, is very long wearing, an important consideration in the present application.

The piston 154 in turn secured to a piston carrying piece 156, as for example, by being cemented at the areas 158 by an epoxy-type cement or similar good bonding agent. Piston carrying piece 156 is formed at its distal end with an enlarged portion 160 so that the entire piston assembly consisting of carrier piece 156 and piston 154 may be retained within slider 136 by means of a threaded slider nut 162. The transverse diameters of the various portions of piston carrier 156 held within the slider nut 162 are somewhat smaller than the inside diameter of the adjacent walls of the slider nut. In consequence of this, a degree of side-to-side or lateral movement, i.e., transverse to the piston axis, is enabled. This is deemed significant in order to compensate for possible misalignment problems that can initially be present or which may develop, e.g. misalignment between the piston axis and the axis of pump chamber 144.

Where the piston 154 passes through plate 140 an alignment cap 164 is provided, the piston being guided in its passage therethrough by a guide bushing 165 of a tough flexible fluorocarbon such as Teflon, Kel-F, or similar products. Thereupon the piston 154 passes through a high pressure seal 166 which is sandwiched between a guide bushing 168 and a back-up ring 170. The high pressure seal 166 may comprise a radially expandable seal, such as for example a spring-loaded seal of this type formed from Teflon and available from the Bal Seal Engineering Company of Tustin, Calif. Similarly, guide bushing 168 is preferably formed of a plastic self-lubricating material, such as Teflon, Kel-F or a similar fluorocarbon. The enlarged view of FIG. 3 also illustrates the two extreme positions of the piston: i.e., its maximum forward displacement or pumping position being indicated as a solid line, and its maximum withdrawal position being indicated by the dotted line position at 171. The piston 154 is actually quite small: a typical diameter is ⅛ inch, with the stroke length being 0.448 inch and the volume displacement being 90 microliters/stroke.

Referring now to the lower eccentric, i.e., the inlet valve eccentric 116, the eccentricity of this circular device about it center 172 is considerably less than the eccentricity of the pump eccentric 112. A lesser eccentricity is required for the valve eccentric 116 because the inlet valve movement, which is ultimately effected by displacement of valve needle 174, is comparatively a quite small movement. In analogy to the description provided with respect to pump eccentric 112, the inlet valve eccentric 116 includes the yoke pieces 176 and 178 which are joined by bolts or other fasteners 180. The yoke rotates about a ball bearing 182 and draws with it the connecting link 184, which in turn displaces (to the right or left in the sense of the drawing) the wrist pin 186. The latter is mounted within a ball bearing 188 and draws with it the valve slider 190.

Figure 4:
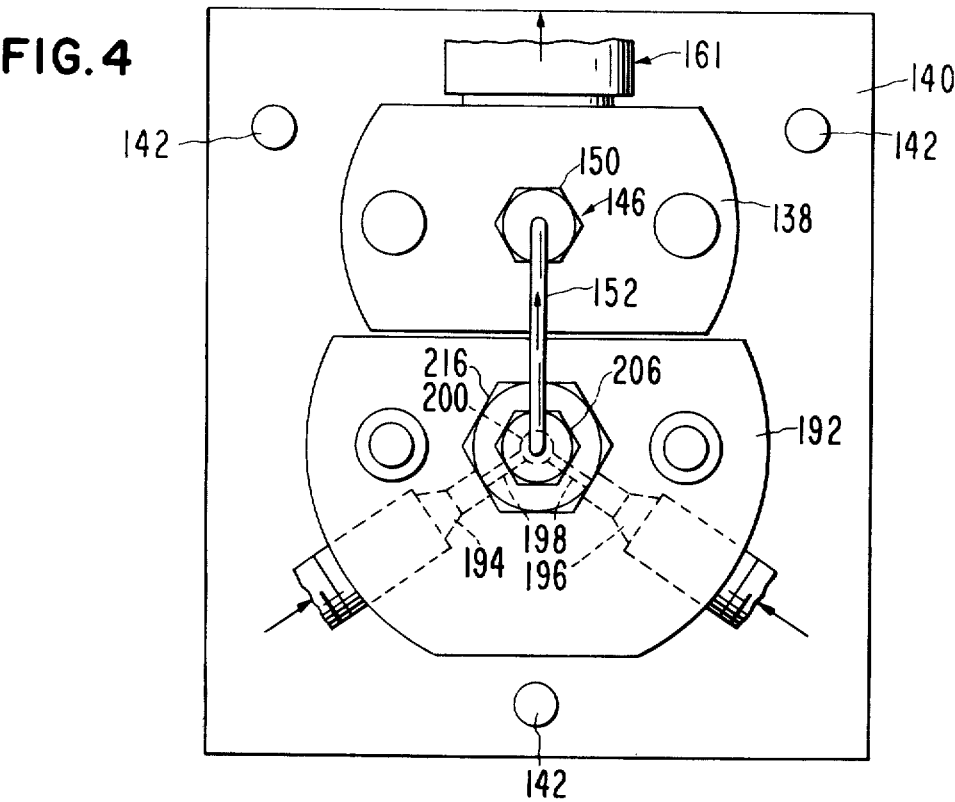
FIG. 4 is an elevational end view of the portions of the present apparatus appearing in FIG. 3.

The mechanical interconnection between valve slider 190 and valve needle 174 is such as to provide controllable play between the two, yet more specifically, an over-travel mechanism is provided between these elements. The manner in which this achieved will shortly become evident; but its purpose may be appreciated by referring to the inlet valve housing 192. Solvent which is to be pumped by the apparatus, is admitted to the housing by means of one or more inlet ports, one of which is seen at 194. This is a simple threaded port, which is thus adapted to receive conventional couplings. In simultaneously considering the end view of FIG. 4, it will be evident that where two such ports are present, the axis of port 194 is actually displaced to one side of the vertical plane; and similarly the axis of port 196 is displaced to the other side of said vertical plane. Accordingly, it will be evident that, in the depictions of FIGS. 2 and 3, inlet port 194 has actually been rotated somewhat from its true plane in order to enable it to be seen in the drawings.

It will thus be clear that the passageway 198 proceeding from inlet port 194 enters inlet chamber 200, from which it will pass into a conduit 202 and thence outward from such chamber through the port 204 at retaining nut 216. Port 204 threadingly receives a connector 206, which conducts the flow into and through the inlet 148 of pump head 138 via the tubular conduit 152.

The entrance to passageway 202 is controlled by the tip 208 of valve neede 174, which tip engages with the valve seat 210. The latter preferably comprises a tough but resilient plastic material, such as for example the Kel-F product previously mentioned. It is important in this connection to appreciate that the seal must, during the pump portion of the cycle herein, withstand high back pressures, i.e., of the order of 5,000 psi. The valve seat 210 adjoins stainless backup ring 212; thence a Teflon O-ring 214 is interfaced between ring 212 and retaining nut 216 defining the aforementioned threaded port 204.

It will be evident that back-and-forth axially directed displacement of the valve needle 174 opens and closes the inlet passage 202. It will further be evident that the needle valve 174 must be closed for a finite period, i.e., during the pumping cycle. Partially be virtue of the overtravel mechanism previously mentioned, all of these aspects of the valve needle movement may be effected. In particular, it will be seen that valve needle 174 is threadingly received within a nut 220 and is retained at its threaded position by means of a locknut 222. A portion 224 of slider 190 contains an opening 226 into which is threaded a screw 228 which is retained by a lock washer 230. The bottom end 232 of nut 220 is separated from the facing end 234 of slider 190 by a spring 236 positioned about portion 224. The spring may comprise a series of Belville washers. A pin 240 passes through one side of nut 220 and engages an axially extending slot at the side of portion 224. The said pin serves purely an anti-rotational function, i.e., it prevents relative rotation between needle 174 and the slider 190 which can otherwise occur during extended use of the present pump and thereby alter the characteristics of the seating of needle 174.

It will be evident from consideration of the construction just indicated that, as slider 190 moves to the right (in the sense of the drawing), the spring member 236 bearing against the end 232 of nut 220, moves the entire assembly to the right, including the valve needle 174. As the tip 208 of the needle approaches its seated position, the spring 236 compresses slightly, so that a small amount of overtravel occurs (as is specifically indicated by the distance 242), which represents a slight degree of movement of portion 224 within the cavity 244 of nut 220. This degree of overtravel, i.e., the time it takes for the slider to move this distance 242, represents the total seating time of the needle. During this period that the needle is seated, the pump stroke is effected; and further, the pump piston 154 actually begins its withdrawal — with a slight delay before the valve needle actually reopens to admit liquid to the pump chamber 144. The purpose of this slight delay in opening is to permit the solvents, which have been severly compressed during pumping, to regain their normal volume; i.e., the objective of this delay is to avoid the possibility of the compressed liquid backing up through the inlet valve. In addition, this delay allows relaxation of stressed mechanical components. Clearly the opening of the needle valve is effected by slider 190 moving to the left (in the sense of the Figure) as soon as the overtravel 242 is taken up by movement in the indicated leftward direction of portion 224. The washer 246 and screw head 245 will be brough to bear against the interior face 250 of nut 220 to then initiate the rearward movement of valve needle 174.

Fluid from the pumping chamber 144 proceeds via an outlet passage 151; and after passing through a sintered metal filter 153, the fluid passes through first and second stage check valves 155 and 157 and thereupon exists from the system by the outlet port 159. The fluid from outlet port 159 proceeds toward the LC column by way of the further elements indicated in FIG. 1

Considering the outlet valve assembly 161 more generally, it is seen to include an upper body 163 and a lower body 175. Lower body 175 is secured to pump head 138 by being threadingly received therein. The first stage check valve 155 consists of a ruby ball 167, which is biased by a spring 169 against a sapphire seat 171. An O-ring 173 is positioned between the sapphire seat and a stainless steel filter-holding piece 177. The filter holding piece is provided with a passage 179 for the fluid, and the sintered metal filter 153 is welded to piece 177.

It will be noted that sintered metal filter 153 is of extended axial length, so that a relatively large volume 189 is provided between the opening of passage 179 and the passage 151 leading to the filter. In consequence, a very extended area of filtering is provided prior to first stage check valve 155, which acts in very effective fashion to prevent particulate matter from passing to either of the check valves stages. This is deemed highly significant for present purposes in that (especially in view of the high pressures utilized in the the present system) even a minor degree of particulate sediment could impair closing; i.e. even a small amount of particular sediment could impair proper seating of the ruby ball valves, with resulting highly detrimental effects on system performance.

Above the first stage check valve 155 already mentioned, is the second sttage check valve 157. In this later instance, the valve again comprises a ruby ball 183 in a further sapphire seat 185 and O-ring 187. In the case of this second stage check valve, the biasing is gravity induced as opposed to the spring biasing of the first stage valve. A small cylindrical stop 191 is positioned atop the ruby ball 183 to limit its upward movement, and thereby to facilitate closing. The stop is provided with grooves extending axially along its periphery so that flow will not be impaired by the ball residing against the ring.

Secured directly beneath coupler 102 upon crank shaft 56 is a flywheel 251, which by storing inertia further damps possible vibrations. Directly affixed atop flywheel 251 is an encoder disc 252, the peripheral portion 254 of which protrudes beyond the flywheel to enable reading thereof. Details of the encoder wheel will be discussed further hereinbelow. Suffice it for present to point out that the wheel carries a series of radially extending slots about the peripheral portion 254, which slots may be read by a optical reader means 256 seen to be positioned at one side of the shaft, so as to permit the peripheral portion 254 to pass in reading relationship therewith. The reading device is, per se, a conventional type of optical switch basically consisting of a light emitting diode (LED) which activates a phototransistor across an airspace or gap in such device. When the light beam is mechanically interrupted, or when the light beam is enabled, the output will change and thus reader means 256 may be appropriately utilized to read the slots in the disc.

It has previously been indicated in the Background portion of the present specification, that single chamber pumps based upon reciprocation of a fluid follower such as a piston, are not unknown in the applications to which the present invention apertains. The pulsating flow problem to which the present invention particularly addresses itself may be appreciated by consideration of FIGS. 5 through 7 herein, which are simplified schematic and graphical depictions of a typical simple prior art device (FIG. 5, further, however, will be subsequently utilized in explaining certain aspects of the present invention). Thus, referring to FIG. 5, a crank 260 and connecting rod 262 appear; the rod is mounted to the crank toward a peripheral point 264. The crank undergoes rotation from a reference line 266, so that the cumulative angle of rotation is $\theta$. The connecting rod 262 at its opposite end is secured at point 268 to a piston 270, which is able to undergo to-and-fro reciprocation in an axial direction within a cylinder 272. Fluid enters the cylinder through a valved inlet 274, and is discharged from the cylinder upon advance of the piston via the valved outlet 276. The diameter of crankshaft 260 is 2R. Its angle of rotation is given by the expression $\theta = \omega t$, and the axial displacement $x$ of piston 270 as a function of time is given by the expression $x = R \cos \omega t$, where $\omega$ is the angular velocity of rotation of crank 260.

Figure 6:
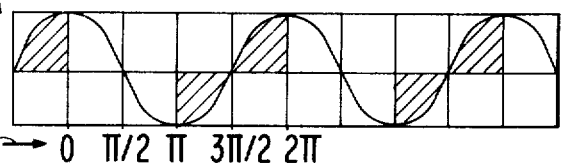
FIGS. 6 and 7 are graphs respectively depicting piston displacement and velocity for the device of FIG. 5.

Referring next to FIG. 6, a graph is set forth indicating the piston 270 displacement $x$ as a function of the angle of rotation $\theta$ of crankshaft 260. The piston displacement, as would be expected, is an approximate sinusoid. Correspondingly, the depiction of FIG. 7, which is a graph of the time derivative of displacement $x$, (i.e., of velocity), is an approximate sinusoid displaced by 90 degrees from the piston displacement $x$. Since the piston velocity will also be proportional to the flow of liquid through the cylinder chamber, the portions of FIG. 7 at 278 and 280, which are respectively identifiable with the fill stroke and with the pump stroke, can be clearly seen. In the case of both FIGS. 6 and 7, the shaded areas under the curves correspond to the pumping portions of the cycle. Thus, it will be abundantly clear that the successive pump strokes in the prior art here discussed, are spaced sinusoidal-shaped pulses.

Figure 7:
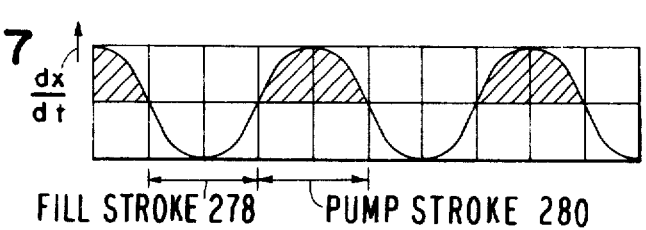

As previously indicated, a fundamental objective of the present construction is to preclude the type of pulsed flow evidenced in FIG. 7. It should in that connection be pointed out that to some extent the prior art has sought to overcome the problems of pulsating flow by the use of flow-smoothingor filtering devices. The difficulty in applying such flow-smoothing of flow-filtering devices to the type of pulsed output indicated in FIG. 7 arises because, while such filtering devices are relatively effective in filtering out or damping the high frequency components of pulsing, they are not markedly effective (or at least are effective to a much lesser degree) where low frequency components are involved. This will be understood by those familiar with mathematical transforms. In particular, the Fourier analysis of the sinusoidal pulses of FIG. 7 will establish that little possibility for improvement by high frequency filtering is present; and thus it will be evident that an unacceptably high degree of pulsating flow will inevitably occur with these prior art arrangements. It will further be appreciated that a particular problem thus arising is the occurrence of an undue degree of detector noise, which can severely impair the operating characteristics of the chromatography system.

Figure 8:
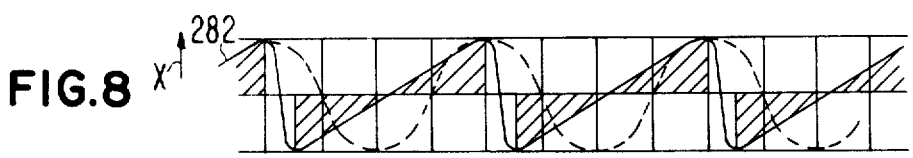
FIG. 8 is a graph illustrating the displacement of a piston of the type shown in FIG. 5 as a function of time, under such conditions that a relatively optimized displacement pattern is effected.

FIG. 8 herein is a graphical depiction of a relatively idealized form of displacement of the piston 270, which form of piston displacement is sought to be effected in order to eliminate the aforementioned pulsing difficulties. The solid line curve 282 once again plots displacement $x$ of the piston as a function of time. The curve may be directly compared with the prior art results of FIGS. 6 and 7; and simultaneously, reference should be further made to FIG. 9 which illustrates (in analogy to FIG. 7) the time derivative of $x$, (i.e., the velocity of piston movement, and thus the liquid flow rate through the cylinder). In order to simplify comparison with the prior art approach, it may be noted that the sinusoids of FIGS. 6 and 7 are plotted as dotted curves on the same coordinate axes. As in the prior curves, the shaded areas under the instant curves correspond to the pumping portion of the cycle.

Figure 9:
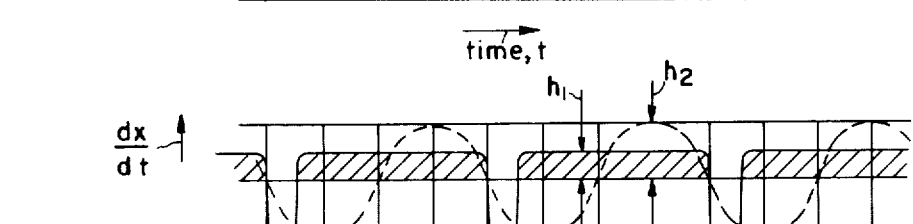
FIG. 9 is a graph illustrating the time derivative of displacement for the piston in the graph of FIG. 8. The showing of this Figure can be regarded as indicating the flow pattern produced during this relatively optimized motion.

It will be seen from FIGS. 8 and 9 that the piston motion sought to be effected is essentially one wherein the piston undergoes a linear change in displacement as a function of time as the piston moves into the cylinder corresponding during the pumping stroke, and wherein the piston at the end of the pumping stroke is rapidly withdrawn in relatively abrupt fashion from the cylinder only to repeat its forward movement into the cylinder — again in linear fashion with respect to time. Correspondingly, the velocity of movement of the piston, i.e., the time derivative of $x$ as seen in FIG. 9, is such that the corresponding liquid pumping is substantially constant for the time duration identified as pump stroke 284, and that at the termination of each pump stroke a very rapid and short-lived fill stroke 286 ensues. Basically therefore, in this idealized arrangement, a series of relatively extended constant flow portions are enabled by the piston movement, with relatively short displacements (representing the fill stroke) being interjected.

While the resulting flow of (FIG. 9) is seen to be much closer to a non-pulsating flow than that of FIG. 7, a further important consequence of the sort of flow pattern indicated in FIG. 9 is that the relatively sharp disruptions in the steady flow (i.e., the relatively sharp fill periods) can be shown by Fourier analysis to include predominantly high frequency components, which are much more amenable to filtering, thus further reducing pulsation in the flow pattern.

Figure 5:
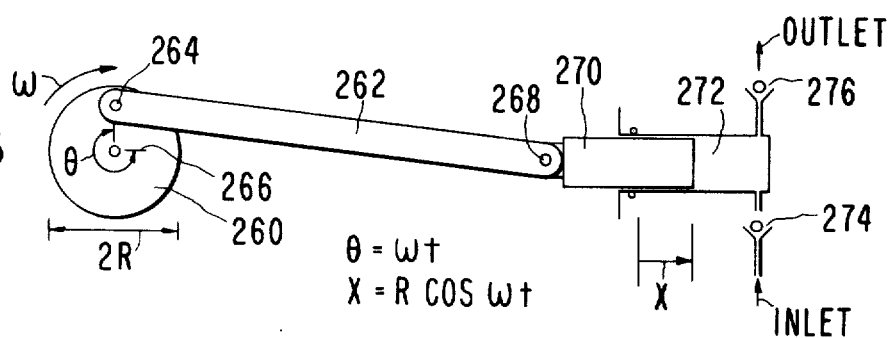
FIG. 5 is a schematic illustration of a typical prior art crankshaft and piston arrangement which effects simple harmonic motion with respect to the piston movement.
Figure 11:
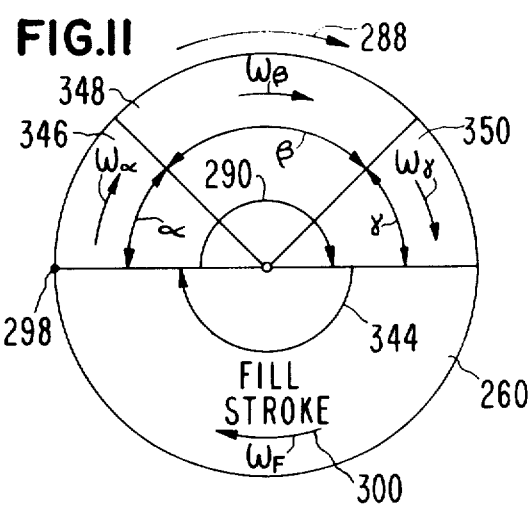
FIG. 11 schematically illustrates crankshaft rotational velocity as a function of crank shaft angle for a preferred embodiment of the present invention.
Figure 10:
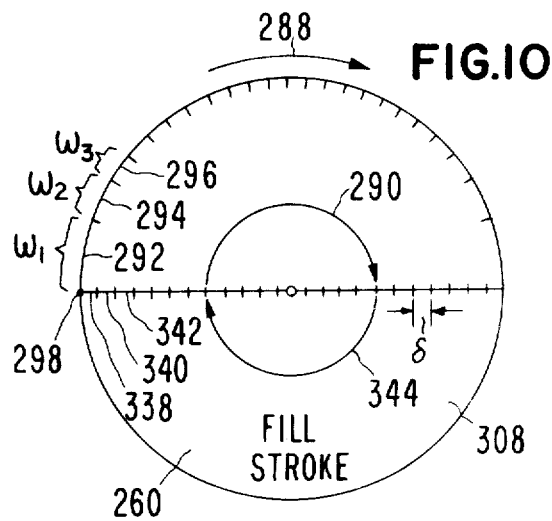
FIG. 10 schematically illustrates an arrangement pursuant to the invention, wherein a stepped change in average crankshaft rotational velocity as a function of angular position, is effected.

FIGS. 10 and 11 indicate in schematic fashion two techniques which may be utilized in accordance with the present invention to produce a piston displacement with respect to time approximating that of FIGS. 8, together with the corresponding flow pattern of FIG. 9. In each of these Figures it may be assumed that the crankshaft 260, in correspondence to the similarly identified crankshaft of FIG. 5, undergoes rotation in the direction 288. This crankshaft may be taken as the schematic equivalent of the shaft 56 of FIG. 2. Similarly, in considering the applicability of the schematic depiction of FIG. 10 to the present invention, the link 262 of FIG. 5 may be regarded as the equivalent of the interlink between the rotating shaft 56 and ultimately the piston 154 of FIGS. 2 and 3. It should be emphasized in this connection that the schematic depiction of FIG. 5 is not a precise physical equivalent of the crank shaft 56 and the attendant linkages to piston 154 and to valve needle 174. Specifically, in the physical structures of FIGS. 2 and 3 the circular cross-sectioned eccentrics 112 and 116, by virtue of the rotation of shaft 56, cause gyration of the yoke pieces effecting reciprocating motion of links 126 and 184, which in turn displace the piston 154 and valve needle 174. However, it will be apparent that the function of the eccentrics and shaft 56 are precisely those of a crank shaft — i.e., with the eccentrics acting as the crank throws — and that accordingly the motions yielded by the mechanisms of FIGS. 2 and 3 may be analyzed by the mathematically equivalent depictions of FIG. 5 and of subsequent description hereinafter referenced to that and the following Figures.

If in FIG. 10 we assume that the rotation of crankshaft 260 through the approximately 180°-angle 290 represents the advancing displacement of the piston, then it will be evident that all that is necessary for the piston displacement to approximate a linear function (of time) is for such crank shaft to undergo a succession of rotations with the average angular velocity through each successive step varying in accordance with the angular position of the shaft. Thus, the initial step through an arbitrarily small angle corresponding to arc 292 may be effected at an average rotational speed $\omega_1$. The next step, which is through the angle of arc 294, will be at a second average angular speed $\omega_2$; and thus the following successive steps (i.e., the steps through the successive angles of arc 296, etc.) will be at average angular velocity $\omega_3$, etc. In each instance, it will be evident (assuming that the linkage attachment point is at 298) that the piston displacement in the direction $x$ will be the projection of the chord joining the end points of the associated arc upon the $x$ axis. This projection will be approximately related to the average angular velocity in the particular sub-interval represented by the appropriate arc portion 292, 294, 296, etc., such that the resulting equal projections 338, 340, 342, etc., represent the distance traveled in an equal interval of time. It will thus be evident that by breaking up the angle 290 into a very large number of arc steps, each step being associated with its appropriate average constant velocity over such step, arbitrarily close approximation to linear displacement for the piston is enabled. This sort of effect can be seen in FIG. 12 which plots the case corresponding to FIG. 10, i.e., where the crankshaft rotates in a plurality of discrete segments each yielding an identical linear advance $\delta$ of the piston.

Figure 12:
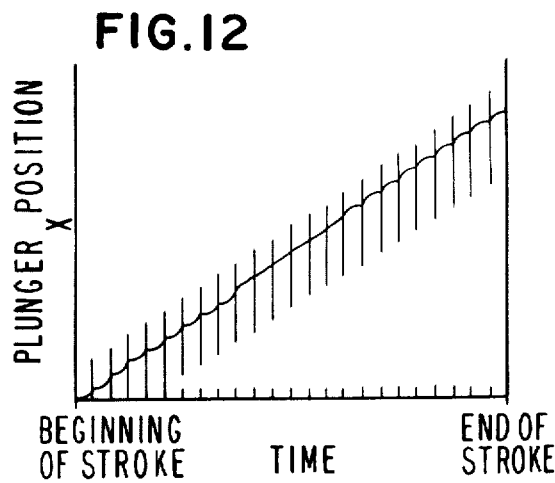
FIG. 12 illustrates a typical result that is achievable by means of the crankshaft angular velocity pattern set forth in FIG. 10.

As will shortly be evident, the present invention is indeed fully appropriate for use with the scheme discussed in FIGS. 10 and 12. As a practical matter, however, and in order to vastly simplify the cost of circuit components and the complexity of the present apparatus, a preferred form of the invention utilizes a relatively small number of changes in angular velocity among several sub-intervals of the pump stroke of the apparatus. This aspect of the invention may be better appreciated by reference to FIG. 11, which is a schematic generally similar to FIG. 10 and having similar purposes. It should be noted in connection with this Figure, as well as in connection with FIG. 10, that the approximately 180°-angle 344 corresponds to the fill stroke of the apparatus; and during the crank rotation corresponding to such fill stroke, a constant angular velocity $\omega_F$ is utilized, which is comparatively very high vis-a-vis the average angular velocities thus far discussed with reference to the pump stroke.

Figure 13:
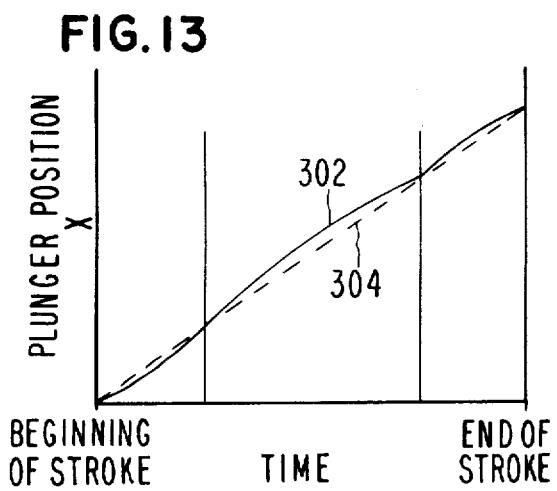
FIG. 13 illustrates a typical displacement pattern achievable where the techniques of the FIG. 11 graphical showing are utilized.

In FIG. 11, the pump stroke is represented by three angular portions, 346, 348, and 350, which in total extend over 180° of the simplified schematic showing. During the first sub-interval, i.e., the interval extending over the angle $\alpha$, the angular velocity of the crankshaft is maintained at a fixed value $\omega_\alpha$. During the second portion, i.e., the interval extending over the angle $\beta$, the angular velocity of the crankshaft is maintained at the value of $\omega_\beta$; and finally, over the last portion 350 corresponding to the end of the pump stroke, i.e., the interval extending over the angle, the angular velocity is maintained at the value $\omega_\gamma$. Basically, it recognized in this tripartite breakup of the selection of angular velocity that, over the midportion of the pump stroke, i.e., within the angle $\beta$, the forward displacement of the pump piston is relatively uniform with respect to time. By making suitable adjustments at the front and rear of the strokes, i.e., in the rotational velocities over the relatively limited angles $\alpha$ and $\gamma$, a fairly good approximation to linear rate displacement may be effected. Thus, a typical curve which is yielded by application of these principles appears in FIG. 13. The solid line 302 represents actual displacement where typical parameters are used, and the dotted line 304 indicates the idealized linear case. It will be evident that the first curve represents a very close approximation to the second.

In FIG. 14 herein a further schematic depiction appears. The representation of this Figure is similar to that discussed in connection with FIGS. 10 and 11, except that in the present instance the Figure introduces certain modifications which enable superior results with the embodiment of the invention illustrated in FIGS. 1 through 4. This Figure may be viewed simultaneously with FIG. 15, which specifically sets forth the fluid flow resulting from the cycling arrangement of FIG. 14 where apparatus in accordance with the invention is utilized. In considering FIG. 14, it may first be noted that the assumed direction of rotation of the crankshaft is in the counter-clockwise direction— this being in accord with standard mathematical convention, but being contrary to the convention used in the prior Figures. Thus, the initial reference line for angular rotation is the axis 310. This axis may also be taken as representing (i.e., when the crankshaft is in that position) the zero time point, as that elapsed time is set forth in FIG. 15. It will be noted basically that throughout the cycle of crankshaft rotation shown in FIG. 14 three differing average rotational speeds are utilized. Associating these rotational speeds with the frequency of pulse repetition provided to stepping motor 52, it may thus be indicated that for the entire fill cycle a fixed frequency $f_0$ is utilized. This means that the rotation of shaft 56 is at a constant rate during the large angle corresponding to $f_0$ in FIG. 14. The frequency $f_0$ is comparatively quite high in order to give the short fill duration which is indicated in FIG. 15. Thus in the typical instance $f_0$ may have a value of 500 pulses per second, which with the typical motor utilized in the present device corresponds to approximately 150 rpm. The point identified as 312 in FIG. 14, which resides on the x axis, represents the point of maximum withdrawal of piston 154 and the point at which the inlet valve 174 closes. The pump stroke now begins with the stepping motor initially continuing to rotate at the speed corresponding to $f_0$, the object of this being to rapidly move the piston from the dead center positions.

At point 314 the shaft begins rotation over a short angular displacement at a rotational speed provided at pulse input rate $f_1$. Thereafter, a second relatively slower speed rotation is effected extending over approximately 90 degrees, the motor being driven by a pulse rate $f_2$. Thereafter, a third relatively short period of rotation at the higher rate provided by input pulses at the frequency $f_1$ ensues. It will be noted that at point 316 the high speed rotational drive is reinitiated by application of pulses at the highest rate $f_0$ for the same purposes previously mentioned. However, it will be noted that although the rearward or fill stroke then begins at point 310, the inlet valve 174 does not actually open for a short delay period — which is indicated by the angle 318. The purpose of this delay (indicated at 319 in FIG. 15) in inlet valve opening has previously been discussed, its objective being to allow for the decompression of the solvent and for relaxation of stressed mechanical components. As has been previously discussed, the specific values of $f_1$ and $f_2$ are predetermined in accordance with the selected flow rate, such information being stored in the read-only memory block 72 in FIG. 1.

Throughout the lower and middle portions of the system flow range, the frequency $f_0$ of the stepping motor drive during the fill portion of the cycle remains constant regardless of the setting of the flow rate. This indeed is a quite distinct aspect of the present system vis a vis prior art systems which, as has been mentioned, are correlated to a mechanical cam operation. It will thus be evident that as the flow rate is set to successively higher values, the average rate of the pumping portion of the cycle increases, but not that of the fill portion. This aspect of the present invention is illustrated by the graph of FIG. 16, which plots the ratio of fill time to total cycle time as a function of flow rate in milliliters per hour for a typical instrument in accordance with the invention. It will be evident from this graphical depiction that as the flow rate approaches a certain value, in this instance as it approaches about 600 milliliters per hour, the fill time moves toward a value of 50% of the total cycle time. (The discontinuity between 590 and 600 ml/hr arises because the instrument flow is only settable in 10 ml/hr increments). As has also been discussed previously, the underlying factor enabling the last result is that, at the relatively high pumping rates, the reciprocation of the piston is so rapid that pulsation effects become insignificant; and one can, in effect, operate at such high pumping rates in a straight forward sinusoidal manner, reminiscent of prior art devices. Of course, as one proceeds beyond the indicated limit of about 600 ml/hr, the same rate of pulse application will be provided throughout the crank shaft 56 rotation. Thus, the frequency $f_o$ of pulse application is no longer used during fill. Actually, the frequencies employed for the higher flow rates are lower than $f_0$. In comparison to the under 600 ml/hr flow, the rotational rate of shaft 56 becomes lower during the fill sub-cycle, although higher in the pump sub-cycle.

A further point that should be emphasized in connection with the invention regards the solenoid actuated proportioning valves 28 and 30. When one considers the manner in which these valves function, it will be clear that they are very fast acting in nature. Each of these valves typically, therefore, has a very short stroke — of the order of 25 thousandths of an inch — and has an opening time in the range of 1 millisecond and a closing time in the range of 3 milliseconds. The valves typically include a so-called soft seal, i.e., a soft seal between the plunger and valve seat; and because of the possibly highly corrosive nature of the materials handled in systems of the present type, the valves preferably are constructed of highly resistant materials, e.g., Teflon or fluoroelastomer, and stainless steel may be used throughout.

In FIG. 17, a perspective view appears of the encoding disc 252 and of the adjacent fly wheel 250, together with the encoder reading head 256. The axis of the pump crankshaft is indicated at 56. The encoding disc per se is seen to comprise an annular disc, the periphery of which is provided with a series of tooth-like cuts or slots, each slot of which therefore extends along a radius of the disc. It will be evident even from FIG. 17 that each slot 322 has an equal width. However, the spacing between slots arises varies as one proceeds about the disc through an angle of 90°.

In FIG. 18, a schematic depiction is set forth which shows approximately to scale the spacing between successive slots 322, which slots are schematically suggested in each instance by the successive lines 324. The basic overall objective of the arrangement indicated is to assure that the spacing between any two successive slots corresponds to an equal incremental displacement of the piston 154. To put this in a somewhat different manner: Presume that the reading head 256 initially detects a first slot at a time $T_0$. The encoding disc 252 affixed to crank shaft 56 continues to turn, and thus reading head 256 detects the following successive slot at a time $T_1$. During the time interval $T_1 - T_0$, the piston 154 will have undergone a certain displacement along its axis. The discreet distance represented by this displacement will accordingly be the same for the angular rotation of the crank shaft 56 between any two successive slots. This phenomenon is well illustrated in FIG. 19. As disc 252 turns in the direction of angle indicia 322 are detected at point 350, with the attachment point for the piston link being at 352. Equal displacements δ along axis 354 occur for the piston (which initially moves in direction 356) corresponding to the appearance of indicia at the detection point 350.

The indicia arrangement provides an exceedingly simple and accurate scheme for directly correlating piston position with the pulses proceeding from reading head 256. This, in turn, enables the very simple and yet highly accurate proportioning technique which has been previously described with reference to operation of the proportioning valves 28 and 30. In essence, all one need do is start counting the pulses derived from rotation of encoder disc 252 during the fill cycle, and divide the totality of fill time represented by the successive number of pulses in accordance with the proportion of solvent A desired in comparison to solvent B. This avoids the use of complex electronic techniques or corresponding mechanical apparatus in order to enable fullly accurate and dependable proportioning operations.

In FIG. 20 a partial plan view appears of the peripheral portion of a further encoding disc 360, which operates on precisely the principles heretofore discussed, except that the disc 360 differs in certain construction details. In particular, the fabrication of the disc 360 is simplified in comparison to the device of FIG. 17. Thus, disc 360 may comprise a very thin metal disc into which are photo-etched the slots 361, which, again, are arranged precisely according to the principles heretofore discussed. While the device of the prior FIG. 17 may require relatively sophisticated machining techniques, the simplified encoder disc shown in FIG. 20 is more readily fabricated by the aforementioned photo-etching methodology — which also is capable of very high precision in yielding proper emplacement of the said slots, including the interspacing therebetween.

Figure 23:
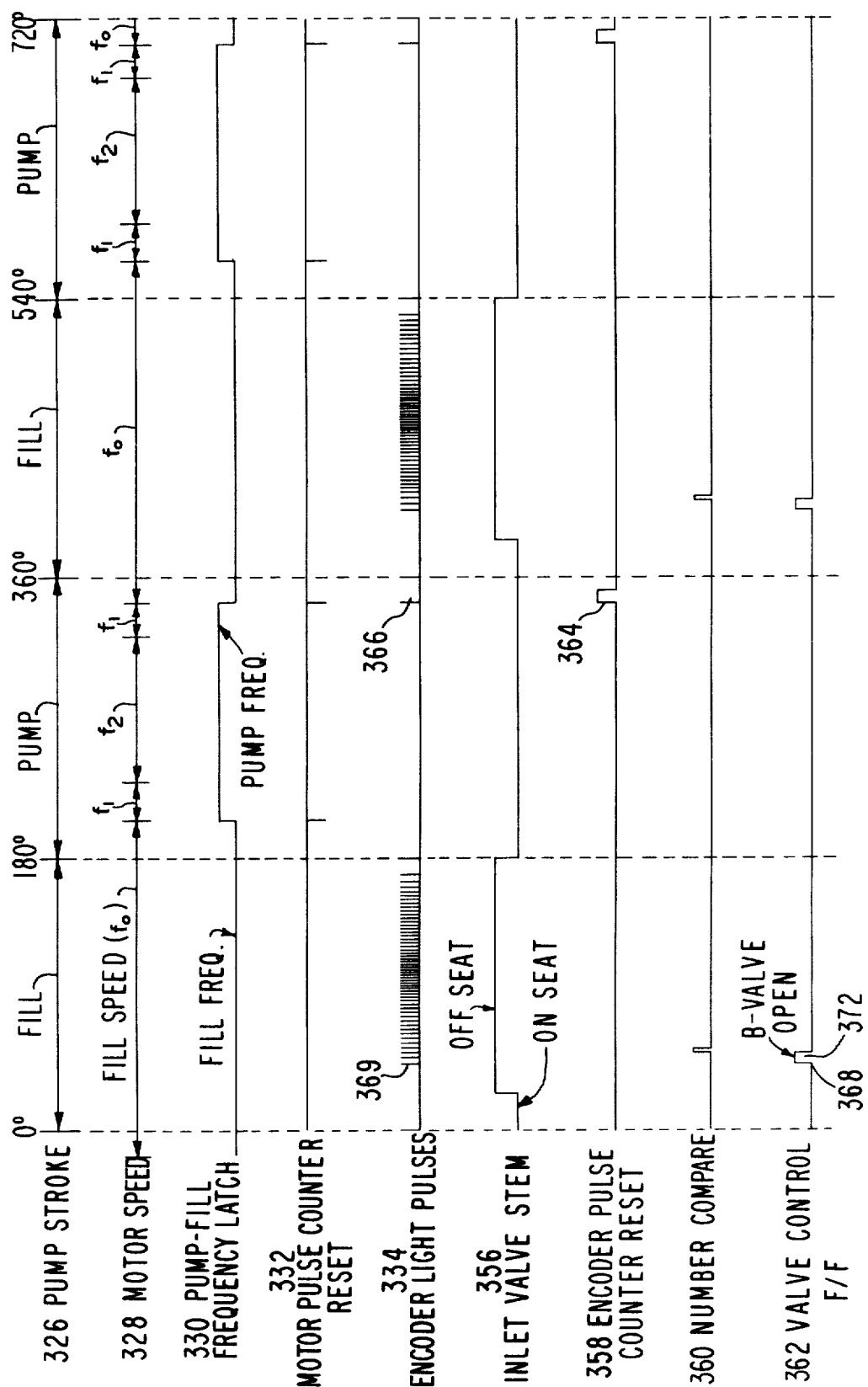
FIG. 23 is a timing diagram setting forth the relationship between certain parameters involved in operation of the invention.

In FIG. 23 herein, a series of timing diagrams are set forth which will prove helpful in understanding the various actions occuring during operation of the present system, including especially the proportioning technique. It will be useful in considering FIG. 23 to simultaneously consider FIG. 14, which can be directly related to the parameters in FIG. 23. Similarly, reference may be usefully had in correlating the timing sequences shown with the overall schematic depiction of FIG. 1.

At the top line 326 of FIG. 23, there is set forth over an extended angular depiction, i.e., for two revolutions (720°), the sequencing of the piston 154 stroke — which, as may be seen by comparing FIG. 14, runs successively through fill and pump cycles, each of 180°. Correspondingly, again by comparison to FIG. 14, the motor speed over the two revolutions, is shown at line 328. Certain aspects of the division of the revolutions with respect to motor speed are increasingly clear from the present Figure: for example, the fact that at the higher fill speed the frequency $f_0$ extends beyond the 180° point for reasons that have previously been indicated, and similarly is reinitiated at a point preceding the 360° point mark.

In the next successive timing graph (at line 330), the pump-fill frequency latch timing is set forth. This in essence constitutes the control signal for maintaining the highest frequency used in the system, i.e., $f_0$.

There is next set forth at line 332 of the timing diagrams for the pump control system, the timing sequences corresponding to motor pulses counter reset. These are the pulses which are indicated as being processed by block 84 in FIG. 1. They basically are synchronization pulses derived from a mark on the encoder disc, and are seen to correspond with the changeover from the $f_0$ to $f_1$ frequency.

At the next successive line of the timing chart, i.e., at line 334, there is set forth the sequence of pulses which derive from the encoder disc 252. The spacing of these pulses precisely corresponds to previous discussion. It is useful to reemphasize here that the successive pulses are spaced in time but represent successively equal displacement increments for the movement of piston 154.

At the following line 356 of FIG. 23, there is set forth a graphical depiction of the position of the inlet valve 174 as a function of the two revolutions indicated. This depiction again may be directly correlated with FIG. 14. Thus, for the reasons previously discussed, the valve starts to open, i.e., moves off its seat, somewhat beyond the 0 degree mark; and then, however, the valve closes at precisely the 180° mark, at which point the pump cycle is initiated.

The timing characteristics enabling the proportioning valve operation of the present system will be better understood by reference to the last three lines, i.e., the graphed representations at lines 358, 360 and 362, of FIG. 23. The timing operations indicated may be regarded as basically included within the province of the valve logic block, i.e., block 85 of FIG. 1. Thus, referring to line 358, it is seen that a pulse 364 enabling counter reset is generated somewhat prior to the 360° crankshaft displacement angle. The generation of this counter reset pulse is initiated by the occurance of the first encoder disc pulse before the 360° mark is reached, i.e., the pulse 366 at line 334 of this Figure. Basically, the reset pulse 364 acts to trigger a one-shot multivibrator, which resets the counter (counter 60 of FIG. 1) for a comparison which will thereafter be made i.e. during the proportioning operation. Thus, referring back to FIG. 1, the value is set in comparator 82 in accordance with the gradient setting of block 76. Dropping down to line 362 of the present Figure, the level of a valve control flip/flop is shown as a function of the angle of crankshaft rotation. Initially, i.e., at angle 0°, the valve A is open. It will be recalled here that valves A and B operate throughout in complementary fashion, i.e., one is always open when the other is closed. Of course, it will be understood that even if valve A is open, the inlet valve 174 will continue to control flow through the system. In any event, it is significant to observe that the period of the valve B opening is not initiated at the 0° mark, but rather at the point 368 which, by comparing the encoder light pulse line 334, will be seen to occur with pulse 369, and close to the 45° point. This is approximately 15° beyond the opening of the inlet valve, as may be seen by comparison of line 356. The objective of not beginning the proportioning operation until some 15° have passed after the inlet valve begins to open, is to permit conditions to quiet down, i.e., to allow accommodation for transients in the flow. Once the valve B is thus opened, flow will continue through it until the value then appearing at the gradient setting and conversion block 76 is achieved, i.e., until an appropriate number of counts from slot counter 60 (FIG. 1) is detected. When this quantity of pulses is counted, the comparator generates a pulse 372 (at line 362) which then acts upon the valve control flip/flop to close valve B and effectively reopen valve A. Thus, the area under the square curve 372 of line 362 represents the "B-valve open" part of the proportioning cycle.

Such pulsations as may yet remain following the outlet of the present pump may be further diminished by means of a pulse damper, such as the damper 40 shown in FIG. 21. The device illustrated has several marked advantages in comparison to prior art mechanisms used for this purpose. Basically, the device consists of an upper block 380 and a lower or inlet block 382. The inlet for damper 40 is at 384 and admits liquid (as already mentioned) proceeding from the pressure monitor 38, and ultimately from the pump 26. An enlarged, generally cylindrically shaped chamber 386 is formed partially in each of the two blocks 380 and 382. The blocks may comprise a metal or other material capable of withstanding the high pressures encountered. An elongated plug 388 of a slightly compressible tough plastic material, preferably Teflon or a similar fluorocarbon, is mounted within the extended chamber 386. A shoulder 390 is formed about the bottom of chamber 386 so that a small mixing space 392 is provided beneath the plug. A small magnetic stirrer 394, in the form of a simple bar magnet (as is known in the art), is positioned at the bottom of space 392 and can be actuated by an externally applied rotating magnetic field to ensure that stirring and agitation of the liquid continues during flow. If desired, the mixing stage could also precede the present device instead of being integrated therewith. The outlet 396 from the damper occurs at the top of block 380. The Teflon plug has cross channels at the top and bottom ends thereof, two of which are seen at 398 and 400, with two additional channels running perpendicular to the two indicated.

During use, the fluid entering inlet 394 proceeds through the mixing space 392, and thence about the flow space provided between the periphery of plug 388 and the slightly spaced internal walls of pieces 380 and 382. Thence, the liquid exits through the outlet 396.

Basically, what occurs in the device of FIG. 21 is that pressure pulsations effect compression an subsequent decompression of the Teflon plug, which is thus able to dissapate the energy of such pulses in a very effective manner. In the past, it has been common to utilize dampers which effectively constituted enlarged volumes, e.g., a canister somewhat similar to the present type might be utilized, but without the plug indicated herein. Such prior are devices introduced an undue amount of volume into the system, which interfered with purging and with the generation of gradient changes.

The pressure monitor 38 referred to in FIG. 1 can comprise a number of well known devices intended for applications of this type. However, in accordance with a further aspect of the present invention, a pressure measuring device is utilized which has several marked advantages, including the fact that it is of very low cost construction, utilizes extremely low dead volume, and, (in addition to measuring the pressure) may serve to provide a degree of further damping in the present environment. The pressure monitor, as thus illustrated in the perspective view of FIG. 22, consists of a helix or spiral 402 of dual parallel running tubing. The inlet for the extended spiral is at 404, and the outlet immediately adjacent thereto is at 406. The last turn of the double helix defines a small bow-shaped section 410. Internal pressure resulting from the fluid passing through the device causes the spiral to partially unwind, which results in an increase in internal volume. The arrows 408 indicate the resultant motion of the center of the terminal bow-like portion 410. The extent of unwinding of the helix is a measure of the internal pressure, and may be coupled to a read-out device. In the illustration of FIG. 22, this comprises a simple needle indicator 412 that is movable over a calibrated scale 414; but other types of linkages can be utilized to increase the apparent motion provided by the phenomenon just discussed. It will further be evident that the increase in internal volume with increasing pressure serves a secondary but important function, namely absorbing pressure pulses which are present in the fluid. The tubing from which the spiral is formed preferably comprises a relatively chemically inert material such as stainless steel or inconel.

While the present invention has been particularly set forth in terms of specific embodiments thereof, it will be understood in view of the present disclosure, that numerous variations upon the invention are now enabled to those skilled in the art, which variations yet reside within the scope of the present invention. Accordingly, the invention is to be broadly construed and limited only by the scope of the claims now appended hereto.

We claim:

1. A high pressure liquid chromatography system comprising:
   at least one reservoir for a liquid mobile phase;
   a liquid chromatographic column;
   conduit means connecting said column to a detector means for sensing the output flowing from said column;
   a high-pressure reciprocating pump means including a pump chamber for enabling flow via connecting means from said pump chamber toward said column;
   structure defining a flow path between said reservoir and said pump chamber;
   inlet valve means in said flow path between said reservoir and said pump chamber; and
   motor means coupled to said pump means for driving same;
   said motor means being mechanically linked to said inlet valve means for actuating said inlet valve means to enable flow of said mobile phase to said pumping chamber.

2. The system in accordance with claim 1 wherein said motor means includes a drive shaft, and wherein a pump crank shaft is coupled to said drive shaft, said inlet valve means being actuatable by said pump crank shaft.

3. The system in accordance with claim 2 including means for actuating said inlet valve means, said actuating means including an inlet valve eccentric carried by said crank shaft and rotatable therewith, and means displaceable by the movement of said eccentric toward and away from the axis of said crank shaft.

4. The system in accordance with claim 3, wherein said inlet valve means includes a valve needle and valve seat; and wherein said means displaced by said valve eccentric includes a slider member reciprocatable along the axis of said valve needle in response to said valve eccentric rotation for displacing said needle to open and close said valve, and overtravel means between said valve needle and said slider means for enabling discontinuity in the axial displacement of said needle to permit a predetermined period of seating thereof.

5. The system in accordance with claim 4, further including means to adjust said overtravel to thereby adjust the seating time of said valve needle.

6. The system in accordance with claim 5, further including a piston reciprocatable in said chamber for pumping said liquid;
   a piston eccentric being mounted for rotation with said crank shaft; and
   means linking said piston to said eccentric for axially reciprocating said piston in response to the rotation of said eccentric about said crank axis.

7. A system in accordance with claim 6 wherein said pump and inlet valve eccentrics are angularly displaced with respect to each other about said crank shaft so as to effect displacement of said inlet valve needle from its seated position subsequent to initiation of withdrawal of said piston from said piston chamber, thereby to delay for a predetermined interval the opening of said inlet valve following the pump stroke of said piston so as to enable decompression of said liquid in said pump chamber.

8. The system in accordance with claim 6 wherein said piston comprises a generally cylindrical rod, and wherein said rod is axially moveable into and from said pumping chamber by a slider means actuated by said pump eccentric;

said rod being secured with respect to said slider means by a means enabling a determinative motion transverse to the axis of said chamber, whereby to accomodate for misalignment between said piston and said chamber.

9. A high-pressure pumping system for use in liquid chromatography, said system comprising:

a reservoir for a liquid;

a liquid chromatographic column;

a positive displacement pump having an inlet and an outlet, said pump enabling flow of said liquid from said reservoir to said column;

valve means for regulating the entry of liquid from said reservoir to the inlet of said pump; and motor means for driving said pump, said motor means being coupled to said inlet valve means by a mechanical linkage for actuation of said valve means and for synchronization of the operation of said valve means with pump displacement.

10. The pumping system of claim 9 wherein said positive displacement pump comprises a chamber and a piston reciprocatable in said chamber.

11. The pumping system of claim 9 wherein said motor means comprises a stepping motor.

12. The pumping system of claim 9 wherein said motor means has a motor drive shaft, and wherein said pump is coupled to a pump crank shaft, said motor drive shaft and said pump crank shaft being coupled directly without gear reduction.

13. The pumping system of claim 12 wherein said positive displacement pump comprises a chamber and a piston reciprocatable in said chamber, and wherein a piston eccentric is mounted for rotation with said pump crank shaft, said piston being linked to said piston eccentric for axial reciprocation of said piston in said chamber in response to the rotation of said piston eccentric.

14. The pumping system of claim 13 further comprising an inlet valve eccentric mounted for rotation with said pump crank shaft, and means displaceable by the movement of said inlet valve eccentric for actuation of said valve means.

15. The pumping system of claim 14 wherein said valve means comprises a valve needle and a valve seat, said means displaceable by the movement of said inlet valve eccentric comprising an elongate member reciprocatable along the axis of said valve needle in response to the rotation of said inlet valve eccentric, the reciprocation of said elongate member serving to open and close said valve means.

16. The pumping system of claim 15 further comprising overtravel means between said valve needle and said elongate member for enabling discontinuity in the axial displacement of said valve needle so as to permit said valve needle to seat in said valve seat for a predetermined length of time.

17. The pumping system of claim 16 further comprising means of adjusting said overtravel means so as to adjust the seating time of said valve needle.

18. The pumping system of claim 17 wherein said piston eccentric and said inlet valve eccentric are angularly displaced with respect to each other about said pump crank shaft so as to effect displacement of said valve needle from its seated position subsequent to initiation of withdrawal of said piston from said chamber, thereby enabling delay of the opening of said valve for a predetermined interval of time following the pump stroke of said pistons, whereby decompression of said liquid in said chamber is enabled.

19. The pumping system of claim 9 wherein said valve means comprises a reciprocating valve.

20. The pumping system of claim 19 wherein said reciprocating valve comprises a moveable elongate needle structure having a tip, and a seat structure for receiving said tip of said needle structure.

21. The pumping system of claim 20 wherein said seat structure is made of a resilient plastic material.

* * * * *